US009730905B2

(12) United States Patent
Gueniche et al.

(10) Patent No.: US 9,730,905 B2
(45) Date of Patent: Aug. 15, 2017

(54) MONOUNSATURATED FATTY ACID FOR PREVENTING AND/OR TREATING SKIN COMPLEXION IMPERFECTIONS

(75) Inventors: Audrey Gueniche, Rueil Malmaison (FR); Isabelle Castiel, Nice (FR)

(73) Assignees: L'OREAL, Paris (FR); NESTEC S.A., Vevey (CH)

( * ) Notice: Subject to any disclaimer, the term of this patent is extended or adjusted under 35 U.S.C. 154(b) by 0 days.

(21) Appl. No.: 13/883,700

(22) PCT Filed: Nov. 3, 2011

(86) PCT No.: PCT/IB2011/054895
§ 371 (c)(1),
(2), (4) Date: Jul. 19, 2013

(87) PCT Pub. No.: WO2012/059880
PCT Pub. Date: May 10, 2012

(65) Prior Publication Data
US 2013/0302297 A1    Nov. 14, 2013

Related U.S. Application Data

(60) Provisional application No. 61/344,909, filed on Nov. 15, 2010.

(30) Foreign Application Priority Data

May 11, 2010  (FR) ..................... 10 59144

(51) Int. Cl.
| A61K 8/37 | (2006.01) |
| A61K 31/201 | (2006.01) |
| A61K 8/36 | (2006.01) |
| A61K 8/92 | (2006.01) |
| A61K 8/99 | (2017.01) |
| A61K 36/185 | (2006.01) |
| A61K 36/23 | (2006.01) |
| A61Q 19/00 | (2006.01) |
| A61K 31/191 | (2006.01) |
| A61K 31/194 | (2006.01) |
| A61K 31/20 | (2006.01) |
| A61K 31/341 | (2006.01) |
| A61K 35/741 | (2015.01) |
| A61K 35/745 | (2015.01) |
| A61K 35/747 | (2015.01) |
| A61K 45/06 | (2006.01) |
| A23K 40/30 | (2016.01) |
| A23K 10/18 | (2016.01) |
| A23K 20/158 | (2016.01) |
| A23K 20/163 | (2016.01) |
| A23K 50/40 | (2016.01) |
| A23K 50/48 | (2016.01) |
| A23P 10/30 | (2016.01) |
| A23L 33/105 | (2016.01) |
| A23L 33/115 | (2016.01) |
| A23L 33/12 | (2016.01) |
| A23L 33/135 | (2016.01) |
| A23L 33/16 | (2016.01) |
| A61K 35/00 | (2006.01) |

(52) U.S. Cl.
CPC ............ *A61K 31/201* (2013.01); *A23K 10/18* (2016.05); *A23K 20/158* (2016.05); *A23K 20/163* (2016.05); *A23K 40/30* (2016.05); *A23K 50/40* (2016.05); *A23K 50/48* (2016.05); *A23L 33/105* (2016.08); *A23L 33/115* (2016.08); *A23L 33/12* (2016.08); *A23L 33/135* (2016.08); *A23L 33/16* (2016.08); *A23P 10/30* (2016.08); *A61K 8/36* (2013.01); *A61K 8/922* (2013.01); *A61K 8/99* (2013.01); *A61K 31/191* (2013.01); *A61K 31/194* (2013.01); *A61K 31/20* (2013.01); *A61K 31/341* (2013.01); *A61K 35/741* (2013.01); *A61K 35/745* (2013.01); *A61K 35/747* (2013.01); *A61K 36/185* (2013.01); *A61K 36/23* (2013.01); *A61K 45/06* (2013.01); *A61Q 19/00* (2013.01); *A23V 2002/00* (2013.01); *A61K 2035/115* (2013.01)

(58) Field of Classification Search
CPC ........................................................ A61K 8/37
See application file for complete search history.

(56) References Cited

U.S. PATENT DOCUMENTS

| 6,365,175 | B1 |  | 4/2002 | Alaluf et al. | |
| RE38,141 | E | * | 6/2003 | Brown | A61K 8/02 424/401 |
| 2001/0033838 | A1 | * | 10/2001 | Farmer | A61K 9/0014 424/115 |

FOREIGN PATENT DOCUMENTS

| EP | 0 709 084 | 5/1996 |
| EP | 1 013 178 | 6/2000 |
| WO | 99 47110 | 9/1999 |

(Continued)

OTHER PUBLICATIONS

Photodamaged Skin, Dr. Joanna Day, Dermatology and Laser Center, https://web.archive.org/web/20070731012500/http://www.drjoannaday.com/skin-PhotodamagedSkin.html, 2007.*

(Continued)

*Primary Examiner* — Rosanne Kosson
(74) *Attorney, Agent, or Firm* — Oblon, McClelland, Maier & Neustadt, L.L.P.

(57) ABSTRACT

The invention relates to the oral or nutraceutical cosmetic use of an effective amount of at least one monounsaturated fatty acid, a salt thereof and/or an ester thereof, as an active agent for treating and/or preventing skin complexion imperfections.

10 Claims, No Drawings

(56) References Cited

FOREIGN PATENT DOCUMENTS

WO    2008 078050    7/2008

OTHER PUBLICATIONS

Tsevegsuren, N. et al., "Geranium Sanguineum (Geraniaceae) Seed Oil: A New Source of Petroselinic and Vernolic Acid", LIPIDS, vol. 39, No. 6, pp. 571-576, (Jun. 2004), XP002638537.
International Search Report issued Feb. 17, 2012 in PCT/IB11/054895 filed Nov. 3, 2011.

* cited by examiner

MONOUNSATURATED FATTY ACID FOR PREVENTING AND/OR TREATING SKIN COMPLEXION IMPERFECTIONS

The present invention relates to the field of cosmetic and/or dermatological products and food supplements for caring for the skin complexion.

More particularly, the present invention proposes the use of a novel active agent for treating and/or preventing esthetic skin defects of the skin complexion. The present invention also relates to processes that are suitable for treating and/or preventing imperfections and uniformity defects of the skin complexion.

BACKGROUND OF THE INVENTION

Many factors may give rise to imperfections in the skin and of its complexion. These skin complexion imperfections are an increasingly frequent reason for consultations in beauty salons or dermatological clinics.

Among the extrinsic factors liable to affect the skin complexion, mention may be made of exposure to sunlight, exposure to temperature and/or moisture variations, and exposure to pollutants or to cigarette smoke. Among the intrinsic factors affecting the skin complexion, mention may be made of stress, fatigue, hormonal changes, dehydration of the epidermis, impairment of the skin's barrier function, aging or excessive secretion of sebum.

What is more, genetic factors may affect the sensitivity of individuals to the external conditions liable to affect the skin complexion.

Thus, certain ethnic groups, for example of Asiatic or African origin, have a skin whose grain is more sensitive and whose complexion may be more easily or more intensely impaired by external conditions such as pollution and cigarette smoke. This is likewise the case for the elderly.

These various factors tend to make the complexion blurry, nonuniform, dull, waxy or yellowish and to bring about or promote the presence of skin impurities or dyschromia.

In their mildest form, these imperfections concern almost everyone, and their frequency is at a maximum during puberty. However, they may appear at an age as early as 7 to 9 and may continue into the 40s, and may especially go into the 60s. Thus, it is common to have imperfections of the skin complexion, especially on the face, such as a blurry, dull and/or nonuniform complexion even after the age of 25. In their mildest form, these complexion imperfections may be manifested mainly by a blurry, dull or nonuniform complexion and the presence of dyschromia or impurities.

In their most severe form, these impairments may occasionally have debilitating psychosocial consequences, liable to lead to isolation, or even to depression or unemployment of the individuals thereby affected.

There is thus a real need to be able to prevent, reduce or treat these skin complexion imperfections.

There is also still a need for novel active agents that can exert an efficient and beneficial action on skin complexion imperfections.

The object of the present invention is to satisfy these needs.

BRIEF SUMMARY OF THE INVENTION

Thus, according to a first of its aspects, the present invention relates to an oral or nutraceutical cosmetic use of an effective amount of at least one monounsaturated fatty acid, a salt thereof and/or an ester thereof, as an active agent for treating and/or preventing skin complexion imperfections.

DETAILED DESCRIPTION OF THE INVENTION

Monounsaturated fatty acids have been described for various applications, such as the moisturization of dry skin in EP 0 709 084 or the treatment of dandruff and itching of the scalp in EP 0 116 439.

WO 01/08651 describes a composition comprising petroselinic acid for controlling the secretion of sebum and for lightening the skin complexion.

U.S. Pat. No. 4,097,604 indicates that a salt of various fatty acids is active against oral cavity pathogens, thus making it possible to reduce the incidence of these bacteria on the onset of periodontitis. The action of these fatty acids is thus limited to the oral flora.

EP 0 355 842 describes a care cream for preventing pigmentation caused by an overproduction of melanin, said cream possibly containing petroselinic acid.

EP 1 013 178 describes the use of petroselinic acid as an anti-inflammatory agent and for treating the signs of aging of the skin, such as wrinkles, flaccid skin and senescence marks.

WO 99/47110 describes a cosmetic method for improving the appearance of the skin using petroselinic acid.

U.S. Pat. No. 6,022,890 describes a composition comprising an α-hydroxy acid, petroselinic acid and a cosmetically acceptable vehicle.

However, none of these documents suggests that the administration of an effective amount of a monounsaturated fatty acid, especially petroselinic acid, to an individual in need thereof could prove to be particularly effective for preventing and/or treating skin complexion imperfections.

The inventors have been able to demonstrate that monounsaturated fatty acids, especially petroselinic acid, lead to a restoration of normal skin tissue in perfect homeostasis, presenting a radiant, youthful and healthy-looking complexion.

Thus, an individual treated according to the invention advantageously sees a reduction or even disappearance of his skin complexion imperfections. The skin complexion may become uniform, without dyschromia or a dull appearance, and free of impurities.

Also advantageously, the invention makes it possible to give the skin, especially facial skin, a radiant and glowing appearance.

For the purposes of the invention, the term "skin" denotes all of an individual's skin, in particular that of a human being, and more particularly the skin of the face, the neck and the neckline. The term "skin" includes surfaces covered with bodily hair.

Preferably, the invention is more particularly suitable for caring for the skin of the face, the neck and the neckline, and preferably for caring for facial skin.

According to yet another of its aspects, a subject of the present invention is an oral cosmetic treatment process that is useful for treating and/or preventing skin complexion imperfections in an individual in need thereof, comprising at least one step of administering to said individual an effective amount of at least one monounsaturated fatty acid, a salt thereof and/or an ester thereof.

The present invention advantageously makes it possible to prevent and/or treat skin complexion imperfections.

According to one embodiment, the invention advantageously makes it possible to prevent and/or treat a blurry, dull and/or nonuniform skin complexion.

According to another embodiment, the invention advantageously makes it possible to prevent and/or treat skin complexion imperfections chosen from pimples, dry patches, dyschromia and blackheads.

According to another embodiment, a use in accordance with the invention advantageously makes it possible to prevent and/or treat a waxy, yellowish or even sickly complexion.

A monounsaturated fatty acid according to the invention is necessarily used in an effective amount, i.e. an amount enabling the fatty acid to manifest its active-agent properties with regard to the skin complexion imperfections to be prevented and/or treated.

For the purposes of the present invention, the term "prevent" means reducing to a lesser degree the risk or probability of occurrence of a given phenomenon, i.e. in the present invention a skin complexion imperfection.

Monounsaturated Fatty Acid

For the purposes of the present invention, the term "monounsaturated fatty acid" means a fatty acid whose hydrocarbon-based chain comprises only one double bond.

Such fatty acids are more particularly fatty acids containing long hydrocarbon-based chains. The monounsaturated fatty acids that are suitable for use in the invention are especially monounsaturated fatty acids comprising a hydrocarbon-based chain containing from 12 to 22 carbon atoms.

The monounsaturated fatty acids that are suitable for use in the invention may be used in acid form or in salt form, or alternatively in the form of derivatives, especially fatty acid esters and amides.

When they are in the form of salts, the monounsaturated fatty acids of the invention are more particularly cosmetically acceptable salts, i.e. inorganic salts, such as ammonium salts, salts of alkali metals such as lithium, potassium or sodium, salts of alkaline-earth metals such as magnesium or calcium, or aluminum salts.

In particular, the monounsaturated fatty acids that are suitable for use in the invention may be in the form of calcium salts.

When they are in the form of esters, the monounsaturated fatty acids of the invention may be esterified with glycerol in mono-, di- or triacyl form, with an alcohol such as methyl and ethyl alcohols, with a sugar, especially a monosaccharide or a disaccharide, a tocopherol, a tocotrienol, a sterol, such as cholesterol or a phytosterol such as β-sitosterol, or with a fatty acid, especially a $C_8$ to $C_{18}$ fatty acid.

It is understood that the choice of the monounsaturated fatty acids of the invention is made taking into account the end use of the composition comprising them.

A monounsaturated fatty acid according to the invention is administered orally.

The monounsaturated fatty acid of the invention, thereof and/or ester thereof may be used in an oral composition in which the content of said monounsaturated fatty acid, salt thereof and/or ester thereof is such that the daily dose ranges from 0.5 to 2500 mg/day and especially from 5 to 500 mg/day.

Among the monounsaturated fatty acids that are suitable for use in the invention, use is made particularly of oleic acid or petroselinic acid. Petroselinic acid is most particularly suitable for use in the invention.

According to one variant of the invention, the monounsaturated fatty acid(s) are used in an isolated form, i.e. after extraction from their source of origin.

According to another variant of the invention, the monounsaturated fatty acid(s) are used in a plant extract such as an oil.

Thus, the invention relates especially to the cosmetic use of an oil rich in monounsaturated fatty acid of the invention, and in particular rich in petroselinic acid.

The oils rich in petroselinic acid are more particularly chosen from *Umbellifera* plant oils.

The term "oil rich in petroselinic acid" means an oil comprising at least 40% petroselinic acid.

Umbelliferae are plants whose flowers are arranged in umbels, and the species that are particularly rich in petroselinic acid are Umbelliferea-Apiacea and Araliaceae. Plants of the genus *Thapsia* are also sources of petroselinic acid (Avato et al., Lipids, 2001, 36, 845).

The species preferably used in the invention are coriander, chervil, carrot, celery, cumin, caraway, parsley and dill.

The *Umbellifera* plant oil used according to the invention may be extracted from the seed of an *Umbellifera* plant, for example by grinding or pressing, followed by refining.

The *Umbellifera* plant oil has a petroselinic acid content that varies according to the *Umbellifera* plant seed from which it is extracted. For the same *Umbellifera* plant, the petroselinic acid content also varies according to the country of origin of the *Umbellifera* plant and according to the extraction, which may be more or less complete.

Petroselinic acid is also an abundant compound (about 48%) of the oil from the seed of *Gernium sanguneum* (Tsevegsuren et al., Lipids, 2004, 39, 571).

According to one embodiment, the monounsaturated fatty acid more particularly under consideration in the invention is petroselinic acid.

In particular, the petroselinic acid may be used in the form of *Umbellifera* plant oil or *Gernium sanguneum* oil.

According to another embodiment, the *Umbellifera* plant oil more particularly under consideration in the invention may be chosen from the seed oils of coriander, chervil, carrot, celery, cumin, caraway, parsley and dill, and mixtures thereof.

Applications

The invention makes it possible to improve, unify or restore the complexion of the skin.

According to one cosmetic embodiment, the invention is directed toward preventing and/or treating skin complexion imperfections.

For the purposes of the invention, the term "skin complexion imperfections" means an impairment in the natural appearance of a healthy skin.

The skin complexion imperfections under consideration in the invention do not include skin impairments resulting from inflammatory phenomena such as inflammatory redness.

The skin complexion imperfections under consideration in the invention do not include skin defects associated with an overproduction of melanin.

The skin complexion imperfections under consideration in the invention do not include skin surface defects, such as roughness or crevasses.

For the purposes of the invention, the skin complexion imperfections do not include complexion lightness defects and the use of the invention is not directed toward lightening the skin complexion or bleaching the skin.

More particularly, the skin complexion imperfections under consideration in the invention may be chosen especially from blurry skin, dull skin and skin of nonuniform complexion, or skin bearing impurities or dyschromia.

For the purposes of the invention, the term "skin impurities" means cysts, comedones or scars with or without dyschromia.

More particularly, the use of a monounsaturated fatty acid according to the invention makes it possible to reveal the radiance of the complexion.

For the purposes of the invention, the expression "reveal the radiance of the skin complexion" cannot in any way be likened to an action directed toward lightening the skin complexion. For the purposes of the invention, the radiance of the skin complexion manifests the natural radiance of the skin complexion characteristic of youthful, healthy skin.

Thus, the invention makes it possible to give a less dull, less blurry and less gray, and more radiant skin complexion.

Galenics

The compositions according to the invention are administered orally. The compositions according to the invention may be in any galenical form normally used according to the route of use.

A composition according to the invention comprises a physiologically or pharmaceutically acceptable medium.

The oral and/or parenteral route has the advantage of acting more globally on the skin as a whole and in its deep layers.

The term "oral composition" means, for example, nutritional, nutraceutical or cosmeceutical compositions, comprising at least one monounsaturated fatty acid according to the invention, a salt thereof and/or an ester thereof.

In the case of a composition suitable for oral administration, the use of an ingestible support is favored. The ingestible support may be of diverse nature depending on the type composition under consideration.

For ingestion, numerous embodiments of oral compositions and especially of food supplements are possible.

The formulation of such compositions may be performed via any usual process known to those skilled in the art for producing, for example, drinkable solutions, sugar-coated tablets, gel capsules, gels, emulsions, tablets to be swallowed or chewed, capsules, especially soft or hard capsules, granules to be dissolved, syrups, solid or liquid foods and sustained-release hydrogels.

Tablets, gel capsules or lozenges, suspensions, oral supplements in dry form and oral supplements in liquid form are suitable, for example, as food support.

In particular, the active agent(s) according to the invention may be incorporated into any form of food supplement or of enriched food, for example food bars, or compacted or non-compacted powders. The powders may be diluted with water, with soda, dairy products or soybean derivatives, or may be incorporated into food bars.

According to one preferred embodiment, a composition according to the invention administered orally may be formulated in the form of a sugar-coated tablet, a gel capsule, a gel, an emulsion, a tablet, a capsule, a hydrogel, a food bar, a compacted or non-compacted powder, a suspension or liquid solution, a confectionery, a fermented milk, a fermented cheese, a chewing gum, a toothpaste or a spray solution.

Examples of suitable food supports include milk, yoghurt, cheese, fermented milks, milk-based fermented products, ice creams, fermented or unfermented cereal-based products, milk-based powders, infant and baby formulas, animal feed, in particular for pets, tablets or lozenges, liquid bacterial suspensions, oral supplements in dry form and oral supplements in liquid form.

The oral compositions may be either in anhydrous form or in aqueous form according to the dermocosmetic indication.

The active agents according to the invention may be formulated with excipients and components that are common for such oral compositions or food supplements, namely, in particular, fatty and/or aqueous components, humectants, thickeners, preserving agents, texture, taste and/or coating agents, antioxidants, preserving agents and colorants that are common in the food sector.

Formulating agents and excipients for oral compositions, and especially for food supplements, are known in this field and will not be the subject of a detailed description herein.

In particular, the composition according to the invention may be a food composition for human consumption. It may in particular be a case of nutritional whole foods, drinks, mineral waters, soups, dietary supplements and replacement foods, nutritional bars, confectioneries, fermented or unfermented milk-based products, yoghurts, milk-based powders, enteral nutritional products, baby and/or infant compositions, fermented or unfermented cereal-based products, ice creams, chocolate, coffee, or "culinary" products such as mayonnaise, tomato puree or salad dressings.

The composition according to the invention may also be intended for animals, especially pets, such as cats and dogs, and may be formulated in the form of feed or food supplements for animals.

Additional Active Agent

A monounsaturated fatty acid according to the invention may advantageously be used in combination with an additional active agent, especially a cosmetic or pharmaceutical active agent.

Advantageously, such an additional cosmetic or pharmaceutical active agent may be intended to exert a cosmetic care or hygiene effect on the skin, the hair, the eyelashes, bodily hair and/or the scalp, and preferentially on the skin.

The additional active agents are chosen by a person skilled in the art so that they do not harm the effect of the monounsaturated fatty acids of the invention.

In particular, an additional active agent that is suitable for use in the invention may be chosen from active agents for treating and/or preventing greasy skin or greasy-prone skin.

According to another embodiment, active agents for preventing and/or treating skin complaints may be combined with a microorganism according to the invention.

As additional active agents that may be used, mention may be made of:

vitamins, such as vitamin A, B5, B6, B8, C, D, E or PP (vitamin B3 or niacin), antioxidants, such as curcuminoids; carotenoids, especially a carotenoid chosen from β-carotene, lycopene and derivatives thereof, such as cis-lycopene or lactolycopene, astaxanthin, zeaxanthin and lutein or compounds containing same, such as wolfberry or lacto-wolfberry; polyphenol compounds, flavonoids such as catechins; hesperidin, proanthocyanidins, anthocyanins, PCOs (procyannidol oligomers); ubiquinones; coffee extracts containing polyphenols and/or diterpenes; chicory extracts; Ginkgo biloba extracts; grape extracts rich in proanthocyanidins; pimento extracts; soybean extracts; cocoa or cocoa milk; pomegranate; Emblica, minerals such as zinc, calcium, magnesium, copper, iron, iodine, manganese, selenium and chromium (III), sugars, amino acids, especially sulfur amino acids such as glutathione precursors, taurine and selenium amino acids, 3 and 6 polyunsaturated fatty acids, prebiotics, chosen especially from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructo-oligosaccharide. More particularly, this prebiotic may comprise a mixture of fructo-oligosaccharide and of inulin, phytosterols, such as resveratrol, hesperidin, and mixtures thereof.

According to one preferred embodiment, a monounsaturated fatty acid according to the invention, a salt thereof and/or an ester thereof may be used in combination with at least one additional cosmetic active agent chosen in particular from vitamin B3, B5, B6, B8, C, E or PP, carotenoids, curcuminoids, niacin, flavonoids, one or more divalent mineral cations, bacteria or bacterial extracts derived from non-photosynthetic, non-fructifying filamentous bacteria, probiotic microorganisms, in particular lactic acid microorganisms, prebiotic nutrients or a mixture of probiotic microorganisms and/or a mixture of prebiotic nutrients.

In particular, use may be made of an antioxidant complex comprising vitamins C and E, and at least one carotenoid, especially a carotenoid chosen from β-carotene, lycopene and derivatives (cis-lycopene, lactolycopene), astaxanthin, zeaxanthin and lutein or compounds containing same such as wolfberry or lactowolfberry, flavonoids such as catechins, hesperidin, proanthocyanidins and anthocyanins, resveratrol, cocoa or cocoa milk, pomegranate and Emblica.

A composition of the invention may also contain one or more divalent mineral cations in various forms.

A divalent mineral cation may thus be in the form of an anhydrous or hydrated mineral or organic salt or a chelated complex. These salts may be, for example, carbonates, bicarbonates, sulfates, glycerophosphates, chlorides, nitrates, acetates, hydroxides, oxides, α-hydroxy acid salts (citrates, tartrates, lactates, malates) or fruit acid salts, or alternatively amino acid salts (aspartate, arginate, fumarate) or fatty acid salts (palmitate, oleate, caseinate, behenate).

A divalent mineral cation may be chosen from manganese, copper and/or zinc or from alkaline-earth metals. As alkaline-earth metals that may be used in the invention, mention may be made of barium, calcium, magnesium, strontium and/or beryllium.

Advantageously, a divalent mineral cation, and especially an alkaline-earth metal, is used in the present invention in salt form. In particular, the salt may be chosen from nitrate, citrate, chloride, gluconate, sulfate, lactate and/or acetate salts.

A divalent mineral cation may also be used in the form of a chelated complex, especially chelated to crystalline or ionized proteins.

A divalent mineral cation may also be in a specific form stored by a microorganism, for example such as a yeast, like selenium yeasts.

According to another embodiment, a composition of the invention may contain non-photosynthetic, non-fructifying filamentous bacteria or bacterial extracts derived from non-photosynthetic, non-fructifying filamentous bacteria as defined according to the classification in Bergey's Manual of Systemic Bacteriology, volume 3, section 23, 9th edition, 1989.

Mention may be made in particular of bacteria belonging to the order of Beggiatoales, and especially bacteria belonging to the genus *Beggiatoa*. Mention may moreover be made of bacteria belonging to the genus *Vitreoscilla*, which is similar to the genus *Beggiatoa*. Among the bacteria that may be used, mention may be made, for example, of *Vitreoscilla beggiatoides* (ATCC 43181) and *Beggiatoa alba* (ATCC33555), and preferentially the use of the extract of *Vitreoscilla filiformis*, in particular with the strain ATCC 15551, metabolites thereof and fractions thereof may be used.

A composition of the invention may also comprise at least one probiotic microorganism, a prebiotic agent or a mixture of probiotic microorganisms and a mixture of prebiotic agents.

Specific examples of probiotic microorganisms that are suitable for use in the invention are *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (LC1, NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp. *bulgaricus, lactis*), *Lactobacillus fermentum, Lactobacillus helveticus, Lactobacillus gallinarum, Lactobacillus gasseri, Lactobacillus johnsonii, Lactobacillus paracasei, Lactobacillus plantarum, Lactobacillus reuteri, Lactobacillus rhamnosus, Lactobacillus salivarius, Lactobacillus alimentarius, Lactobacillus curvatus, Lactobacillus casei* subsp. *casei, Lactobacillus sake, Lactococcus lactis, Enterococcus faecalis* or *faecium, Lactococcus lactis* subsp. *lactis* or *cremoris, Leuconostoc mesenteroides* subsp. *dextranicum, Pediococcus acidilactici, Sporolactobacillus inulinus, Streptococcus salvarius* subsp. *thermophilus, Streptococcus thermophilus, Staphylococcus carnosus, Staphylococcus xylosus, Saccharomyces* (*cerevisiae* or *boulardii*), *Bacillus* (*cereus* var. *toyo* or *subtilis*), *Bacillus coagulans, Bacillus licheniformis, Escherichia coli* strain *nissle, Propionibacterium freudenreichii*, and mixtures thereof.

The microorganisms may be formulated in the form of powders, i.e. in a dry form, or in the form of suspensions or solutions.

More particularly, they may be probiotic microorganisms chosen from microorganisms of the genus *Lactobacillus* sp. and/or *Bifidobacterium* sp., a fraction thereof and/or a metabolite thereof. As illustrations of these microorganisms, mention may be made more particularly of *Lactobacillus johnsonii, Lactobacillus reuteri, Lactobacillus rhamnosus, Lactobacillus paracasei, Lactobacillus casei, Bifidobacterium bifidum, Bifidobacterium breve, Bifidobacterium longum, Bifidobacterium animalis, Bifidobacterium lactis, Bifidobacterium infantis, Bifidobacterium adolescentis* and *Bifidobacterium pseudocatenulatum*, and mixtures thereof.

The species that are most particularly suitable for use are *Lactobacillus johnsonii, Lactobacillus paracasei, Bifidobacterium adolescentis, Bifidobacterium longum* and *Bifidobacterium lactis* NCC 2818 (also known as Bb12 ATCC 27536), which were deposited, respectively, according to the treaty of Budapest, at the Institut Pasteur (28, rue du Docteur Roux, F-75024 Paris cedex 15) on Jun. 30, 1992, Jan. 12, 1999, Apr. 15, 1999, Apr. 15, 1999 and Jun. 7, 2005 under the following designations CNCM I-1225, CNCM I-2116, CNCM I-2168 and CNCM I-2170 and CNCM I-3446, and the genus *Bifidobacterium longum* (BB536). The strain of *Bifidobacterium lactis* CNCM I-3446 may be obtained from Hansen (Chr. Hansen A/S, 10-12 Boege Alle, P.O. Box 407, DK-2970 Hoersholm, Denmark).

According to one particular embodiment of the invention, the composition comprises at least two different microorganisms, which are especially probiotic, and/or metabolites and/or fractions thereof. These microorganisms may differ by their nature, for example bacterium and fungus, or alternatively by their family, their genus or their species, or only by their strain.

The prebiotic agents that are suitable for use in the invention may be chosen from oligosaccharides, produced from glucose, galactose, xylose, maltose, sucrose, lactose, starch, xylan, hemicellulose, inulin, gums of acacia type, for example, or a mixture thereof. More particularly, the oligosaccharide comprises at least one fructo-oligosaccharide. More particularly, this prebiotic may comprise a mixture of fructo-oligosaccharide and of inulin.

A composition of the invention may also advantageously contain polyunsaturated fatty acids chosen especially from ω-3 fatty acids and ω-6 fatty acids.

In particular, the unsaturated fatty acids that are suitable for use in the invention may be chosen from fatty acids comprising from 18 to 22 carbon atoms, in particular polyunsaturated fatty acids, and especially ω-3 and ω-6 fatty acids.

Among the polyunsaturated fatty acids of the ω-6 series that may be used in a composition of the invention, mention may be made in particular of linoleic acid containing 18 carbon atoms and two unsaturations (18:2 ω-6), γ-linolenic acid containing 18 carbon atoms and three unsaturations (18:3 ω-6), di-homo-γ-linolenic acid containing 20 carbon atoms and three unsaturations (20:3 ω-6), arachidonic acid, 5,8,11,14-eicosatetraenoic acid (20:4 ω-6) and docosatetraenoic acid (22:4, ω-6).

The polyunsaturated fatty acids of the ω-3 series may be chosen especially from α-linolenic acid (18:3 ω-3), stearidonic acid (18:4 ω-3), 5,8,11,14,17-eicosapentaenoic acid or EPA (20:5 ω-3), 4,7,10,13,16,19-docosahexaenoic acid or DHA (22:6 ω-3), docosapentaenoic acid (22:5 ω-3) and n-butyl-5,11,14-eicosatrienoic acid.

α-Linolenic acid, γ-linolenic acid, stearidonic acid, eicosapentaenoic acid, docosahexaenoic acid, mixtures thereof or extracts comprising them will be most particularly suitable for use in the invention.

The sources of γ-linolenic acid may be chosen from plant oils, for instance evening-primrose oil, borage oil, blackcurrant pip oil, Ecchium oil and hemp oil, and extracts of the microalga spirulina (*Spirulina maxima* and *Spirulina platensis*).

Plant oils from walnut, hazelnut, almond (*Juglans regia*), coriander, soybean (*Glycina max*), rapeseed (*Brassica napus*), chia, flax, musk rose and fish oils, for example, are rich in polyunsaturated fatty acids of the ω-3 series. ω-3 polyunsaturated fatty acids may also be found in zooplankton, crustaceans/molluscs and fish.

Fish oils are the main industrial source of EPA and DHA.

Microalgal biomass may also constitute a raw material for the extraction of ω-3 unsaturated fatty acids.

Thus, a polyunsaturated fatty acid may be used in a composition of the invention in the form of at least one oil chosen from evening-primrose oil, borage oil, blackcurrant pip oil, walnut oil, soybean oil, fish oil, sunflower oil, wheat germ oil, hemp oil, fenugreek oil, musk rose oil, Ecchium oil, argan oil, baobab oil, rice bran oil, sesame oil, almond oil, walnut oil, hazelnut oil, chia oil, flax oil, musk rose oil, olive oil, avocado oil, safflower oil, coriander oil and/or oil extracted from microalgal biomass (for example *spirulina*) or extracted from zooplankton.

According to one embodiment, a composition of the invention may comprise additional hydrophilic active agents. Hydrophilic active agents that may be used include proteins or protein hydrolysates, amino acids, polyols, especially of $C_2$ to $C_{10}$, for instance glycerol, sorbitol, butylene glycol or polyethylene glycol, urea, allantoin, sugars and sugar derivatives, water-soluble vitamins, starch, and bacterial or plant extracts, for instance those from *Aloe vera*.

According to another embodiment, a composition of the invention may also comprise a lipophilic active agent.

Lipophilic active agents that may be used include retinol (vitamin A) and derivatives thereof, tocopherol (vitamin E) and derivatives thereof, ceramides and essential oils.

The active agents according to the invention may also be combined with active agents intended especially for preventing and/or treating skin complaints.

According to another embodiment, use may also be made of active agents
  which participate in the cohesion of the dermis, for instance glucosamine, rosemary, carnitine, blueberry, sage, spinach, strawberry, green coffee or apple,
  which aid in cell renewal, for instance retinoids and plant hormones, such as daidzein or diosgenin,
  of anti-inflammatory valency, for instance hesperidin or lactoferrin,
  pro-desquamating agents,
  antioxidants,
  antiseborrheic agents,
  antibacterial agents such as antibiotics, for instance erythromycin.

Process

According to another of its aspects, the present invention relates to an oral cosmetic process for treating the skin complexion, and/or associated esthetic skin disorders, which may be used especially by administering the cosmetic compositions as defined above, according to the usual technique for using these compositions.

According to one embodiment, the invention relates to an oral cosmetic process that is useful for preventing and/or treating skin complexion imperfections in an individual in need thereof, comprising at least one step of administering to said individual at least an effective amount of a monounsaturated fatty acid, a salt thereof and/or an ester thereof, and in particular petroselinic acid.

A process according to the invention may comprise a step that consists in observing a reduction or even disappearance of the skin complexion imperfections.

According to one embodiment, a process of the invention may preferably be applied to an elderly individual, an adult woman, an individual with skin of Asiatic type or an individual with skin of African type.

Advantageously, the application of a process of the invention may reduce or even eliminate skin impurities, and preferably from facial skin, restore a homogeneous, unified complexion and/or a complexion not having a dull appearance, and promote a radiant complexion.

A cosmetic process according to the invention may be performed especially by administering a food composition as defined above.

A process of the invention may be performed daily, for example, for example at a rate of one administration a day or of one administration twice a day, for example once in the morning and once in the evening.

A cosmetic process according to the invention may be performed via oral administration, for example by daily administration of a composition formulated, for example, in the form of gel capsules, gels, lotions, sugar-coated tablets, emulsions, tablets, capsules or drinkable vials, in an adequate amount and number, according to their form.

An effective amount of monounsaturated fatty acid may be administered in a single dose per day or in fractional doses over the day, for example two to three times per day.

A process according to the invention may advantageously comprise a single administration.

A cosmetic process of the invention may be performed over a period of time ranging from one week to several weeks, or even several months, this period moreover possibly being repeated after periods without treatment, for several months or even several years.

By way of example, the administration of an active agent according to the invention may be repeated, for example, two to three times per day, or more, and generally over a prolonged period of at least 4 weeks, or even 4 to 15 weeks, with, where appropriate, one or more periods of stoppage.

An oral cosmetic process may be performed over a time period ranging from one week to several weeks, or even several months, this period moreover possibly being repeated after periods without treatment, for several months or even several years.

By way of example, the oral administration of a monounsaturated fatty acid according to the invention may be performed at a rate, for example, of 3 times per day, more generally over a prolonged period of at least 4 weeks, or even 4 to 15 weeks, optionally comprising one or more periods of stoppage or being repeated after a period of stoppage.

In the description and in the examples that follow, unless otherwise indicated, the percentages are weight percentages and the ranges of values written in the form "between . . . and . . . " include the stated lower and upper limits. The ingredients are mixed, before being formulated, in the order and under conditions that may readily be determined by a person skilled in the art.

The examples below are given as nonlimiting illustrations of the field of the invention.

EXAMPLES

Example 1

Oral Compositions

Example 1A: Stick in Powder Form

| Active principle | |
|---|---|
| Lactobacillus paracasei ST11 | $10^{10}$ cfu |
| Bifidobacterium lactis Bb12 | $10^{10}$ cfu |
| Calcium citrate | 50 mg |
| Petroselinic acid | 100 mg |
| Excipient | |
| Xanthan gum | 0.8 mg |
| Sodium benzoate | 0.2 mg |
| Maltodextrin | qs 30 g |

One stick can be taken per day.

Taking such a stick daily for about a week makes it possible to give the skin a uniform and luminous complexion.

Example 1B: Stick in Powder Form

| Active principle | |
|---|---|
| Magnesium gluconate | 50 |
| Lactobacillus paracasei ST11 | $5 \times 10^8$ cfu |
| Bifidobacterium lactis Bb12 | $5 \times 10^8$ cfu |
| Calcium citrate | 200 |
| Coriander oil | 250 |
| Excipient | |
| Xanthan gum | 0.8 mg |
| Sodium benzoate | 0.2 mg |
| Maltodextrin | qs 30 g |

One stick can be taken per day.

Taking such a stick daily for about one week makes it possible to significantly reduce dyschromia and to give the skin a uniform, luminous and radiant complexion.

Example 1C: Capsule

| Active principle | mg/capsule |
|---|---|
| Coriander oil | 150 |
| Vitamin C | 60 |
| Magnesium stearate | 0.02 |

One to three of these capsules may be taken per day.

Taking such a capsule daily for about one week makes it possible to significantly reduce dyschromia, redness and skin imperfections and to give the skin a uniform, luminous and radiant complexion.

Example 1D: Formulation of Sugar-Coated Tablet Type

| | mg/coated tablet |
|---|---|
| Active materials | |
| Coriander oil | 550 |
| Excipient of the core of the coated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Coloring agent | 5 |

This type of sugar-coated tablet may be taken 1 to 3 times per day.

Taking such a sugar-coated tablet daily for about one week makes it possible to significantly reduce dyschromia and skin imperfections and to give the skin a uniform, luminous and radiant complexion.

Example 1E: Formulation of Sugar-Coated Tablet Type

|  | mg/coated tablet |
|---|---|
| Active materials | |
| Coriander oil | 250 |
| *Lactobacillus johnsonii* | $10^9$ cfu |
| Excipient of the core of the coated tablet | |
| Microcrystalline cellulose | 70 |
| Encompress ™ | 60 |
| Magnesium stearate | 3 |
| Anhydrous colloidal silica | 1 |
| Coating agent | |
| Shellac | 5 |
| Talc | 61 |
| Sucrose | 250 |
| Polyvidone | 6 |
| Titanium dioxide | 0.3 |
| Coloring agent | 5 |

This type of sugar-coated tablet may be taken 1 to 3 times per day.

Taking such a sugar-coated tablet daily for about one week makes it possible to significantly reduce dyschromia and to give the skin a uniform, luminous and radiant complexion.

The invention claimed is:

1. A cosmetic method for revealing the radiance of the skin complexion comprising orally administering an effective amount of at least one monounsaturated fatty acid, a salt thereof and/or an ester thereof to a subject in need thereof, said complexion being affected by excessive secretion of sebum.

2. The method of claim 1, in which the skin is the skin of the face, the neck and/or the neckline.

3. The method of claim 1, in which said monounsaturated fatty acid, salt thereof and/or ester thereof is used in an isolated form or in a plant extract.

4. The method of claim 1, in which the monounsaturated fatty acid, salt thereof and/or ester thereof is used in an oral composition, and in which the content of said monounsaturated fatty acid, salt thereof and/or ester thereof is such that the daily dose ranges from 0.5 to 2500 mg/day.

5. The method of claim 1, in which said monounsaturated fatty acid is petroselinic acid.

6. The method of claim 5, in which said petroselinic acid is used in the form of an oil from an *Umbellifera* plant or from *Geranium sanguineum*.

7. The method of claim 6, in which said *Umbellifera* plant oil is chosen from the seed oils of coriander, chervil, carrot, celery, cumin, caraway, parsley and dill, and mixtures thereof.

8. The method of claim 1, in which said monounsaturated fatty acid is used in combination with at least one additional cosmetic active agent, chosen from vitamin B3, B5, B6, B8, C, or E, carotenoids, curcuminoids, niacin, flavonoids, one or more divalent mineral cations, bacteria or bacterial extracts derived from non-photosynthetic, filamentous bacteria, and probiotic microorganisms.

9. The method of claim 8, in which said probiotic microorganism is chosen from microorganisms of the genus *Lactobacillus* or *Bifidobacterium*.

10. The method of claim 8, in which the probiotic microorganism is a lactic acid bacterium.

* * * * *